United States Patent [19]
Gao et al.

[11] Patent Number: 5,495,054
[45] Date of Patent: Feb. 27, 1996

[54] TETRAHYDROINDENO[1,2-D][1,3,2] OXAZABOROLES AND THEIR USE AS ENANTIOSELECTIVE CATALYSTS

[75] Inventors: Yun Gao, Southborough; Yaping Hong, Worcester; Charles M. Zepp, Berlin, all of Mass.

[73] Assignee: Sepracor, Inc., Marlborough, Mass.

[21] Appl. No.: 250,821

[22] Filed: May 31, 1994

[51] Int. Cl.$^6$ .......................... C07C 37/01; C07C 29/143
[52] U.S. Cl. .......................... 568/799; 568/814; 568/837; 568/881; 546/344; 548/562; 549/78; 556/143
[58] Field of Search .................................... 568/799, 881

[56] References Cited

U.S. PATENT DOCUMENTS

| | | | |
|---|---|---|---|
| 4,943,635 | 7/1990 | Corey | 546/13 |
| 5,039,802 | 8/1991 | Blacklock et al. | 546/165 |
| 5,157,129 | 10/1992 | Blacklock et al. | 549/23 |
| 5,189,177 | 2/1993 | Blacklock et al. | 548/405 |
| 5,264,585 | 11/1993 | Blacklock et al. | 548/405 |

FOREIGN PATENT DOCUMENTS

| | | |
|---|---|---|
| 93/23408 | 11/1993 | European Pat. Off. . |
| WO94/26751 | 11/1994 | WIPO . |

OTHER PUBLICATIONS

Didier et al. "Chemo–Enzymatic Synthesis of 1,2- and 1,3- Amino–Alcohols and . . . " *Tetrahedron* 47, 4941–4958 (1991).
Quallich et al. "Diphenyloxazaborolidine A New Catalyst For Enantioselective . . . " *Tetrahedron Letters* 34, 4145–4148 (1993).
Corey et al. "An Efficient and Catalytically Enantioselective Route to (S)–(–)–Phenyloxirane" *J. Org. Chem.* 53, 2861–2863 (1988).
Quallich et al. "In Situ Oxazaborolidines, Practical Enantioselective Hydride Reagents" *SYNLETT* 1993, 929–930 Dec.
Deloux et al. "Asymmetric Boron–Catalyzed Reactions" *Chemical Reviews* 93, 763–784 (1993).
Wallbaum et al. "Asymmetric Synthesis With Chiral Oxazaborolidines" *Tetrahedron: Asymmetry* 3, 1475–1504 (1992).
Singh "Practical and Useful Methods for the Enantioselective Reduction . . . " *Synthesis*, 605–617 (1992).
Martens et al. "Enantioselective catalytic borane reductions of achiral . . . " *Tetrahedron: Asymmetry* 3, 347–350 (1992).
Shaban et al. "Behavior of 2–bromo–1–indanol towards some amines" *Orient. J. Chem.* 3(2), 165–169 (1987).

*Primary Examiner*—Joseph Paul Brust
*Assistant Examiner*—Laura L. Stockton
*Attorney, Agent, or Firm*—Heslin & Rothenberg

[57] ABSTRACT

A method for the enantioselective reduction of prochiral ketones using catalytic amounts of tetrahydroindeno[1,2-d][1,3,2] oxazaboroles of formula II is disclosed.

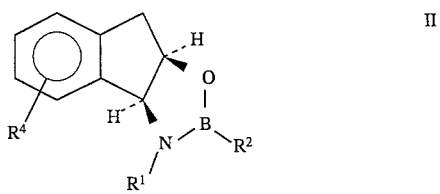

The oxazaboroles can be generated in situ from the corresponding cis-1-amino-2-indanols or imino indanols (III)

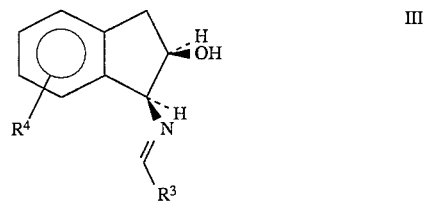

Novel compounds of formulas II and III are also disclosed.

11 Claims, No Drawings

TETRAHYDROINDENO[ 1,2-D] [ 1,3,2] OXAZABOROLES AND THEIR USE AS ENANTIOSELECTIVE CATALYSTS

FIELD OF THE INVENTION

This invention relates to a new class of oxazaborolidines prepared from cis-1-amino-2-indanol derivatives, and to their use as catalysts in the enantioselective reduction of prochiral ketones using a borane reducing agent.

BACKGROUND OF THE INVENTION

The enantioselective reduction of prochiral ketones to give optically active alcohols has been extensively studied, and several reagents have been developed for this transformation. For example, Corey (U.S. Pat. No. 4,943,635) and Blacklock et al. (U.S. Pat. No. 5,039,802) have disclosed one series of oxazaborolidine catalysts derived from (S)- or (R)-2-(diphenylhydroxy methyl)pyrrolidine. These oxazaborolidines are disubstituted at the carbon atom attached directly to the oxygen atom of the oxazaborole, and it has been observed that when the α-carbon atom is not disubstituted, the enantioselectivity of the reduction is much lower. [See Martens, et al., *Tetrahedron: Asymmetry* 3, 347–350 (1992).]

Didier, et al., [*Tetrahedron*, 47, 4941–4958 (1991)] have studied the enantioselective reduction of acetophenone and the corresponding oxime methyl ether with borane in the presence of chiral amino alcohols including cis-1-amino-2-indanol. Didier stated that, under the conditions of their reaction, "With stoichiometric amounts of the ligand, all the reductions of acetophenone required more time than the reduction with borane alone . . . Consequently no system was found to be efficient with catalytic amounts of ligand." They concluded that "it seems, as shown in previous works, that disubstitution in [the] α-position of the hydroxyl group was necessary to attain high selectivities as well as good catalytic effects."

Quallich has disclosed a new class of oxazaborolidine catalysts derived from optically pure 1,2-diphenyl-2-aminoethanols [PCT WO 93/23408; *Tetrahedron Lett* 34, 4145–4148 (1993) and *Synlett* 1993, 929].

The known methods suffer from one or more of the following drawbacks: (a) unacceptable amounts of the undesired enantiomer present as an impurity with the product; (b) low yields of alcohol; (c) difficulty of carrying out the reaction; (d) expense of preparing the catalyst; (e) difficulty in preparing the catalyst; or (f) inapplicability to a wide range of substituted prochiral ketones.

It is therefore an object of this invention to provide chiral oxazaborolidine compounds which are capable of directing the enantioselective reduction of prochiral ketones to generate substantially enantiomerically pure alcohols.

It is a further object of this invention to provide chiral oxazaborolidine compounds which are easily prepared from relatively inexpensive starting materials or readily available starting materials.

It is a still further object of this invention to provide a method of using these chiral oxazaborolidine compounds as catalysts for the enantioselective reduction of prochiral ketones to afford substantially enantiomerically pure alcohols.

SUMMARY OF THE INVENTION

In a first aspect, this invention relates to a method for the enantiospecific reduction of a prochiral ketone. The method comprises reacting the prochiral ketone with a borane reducing agent in an inert solvent in the presence of a catalytic amount of a compound chosen from the group consisting of

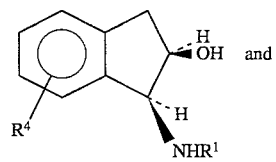

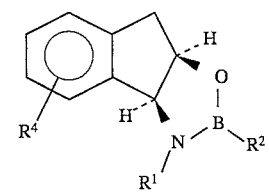

wherein $R^1$ is hydrogen, alkyl, arylmethylene or heteroarylmethylene; $R^2$ is hydrogen, alkyl, benzyl, phenyl or substituted phenyl; and $R^4$ is hydrogen, alkyl, aryl, halo, nitro or alkoxy. Preferred borane reducing agents are borane-methyl sulfide and borane-THF. Preferred oxazaborolidines are (a) those in which $R^2$ is hydrogen, methyl, butyl or phenyl and $R^4$ is hydrogen; and (b) those in which $R^1$ is hydrogen and $R^2$ is hydrogen, methyl, butyl or phenyl.

The ketone may be of the formula IV

wherein Ar is aryl or substituted aryl and $R^5$ is alkyl, hydrogen or halogen. In a preferred embodiment, Ar is phenyl, alkylphenyl, chlorophenyl, hydroxyphenyl, alkoxyphenyl, nitrophenyl or naphthyl.

In another aspect, the invention relates to a process for the enantioselective reduction of a prochiral ketone comprising (a) combining at least one equivalent of a borane reducing agent with a compound of formula III

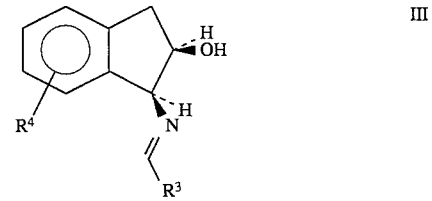

wherein $R^3$ is alkyl, aryl or heteroaryl and $R^4$ is hydrogen, alkyl, aryl, halo or alkoxy, in an inert solvent to provide a catalyst mixture; and (b) adding more than one equivalent of a prochiral ketone and a corresponding amount of a borane reducing agent to said catalyst mixture.

In a preferred embodiment, $R^3$ is phenyl, furan or pyrrole. As before, preferred borane reducing agents are borane-methyl sulfide and borane-THF, and the ketone may be of the formula IV

Preferably, Ar is phenyl, alkylphenyl, chlorophenyl, hydroxyphenyl, alkoxyphenyl, nitrophenyl or naphthyl.

In another aspect, the invention relates to a compound of formula III

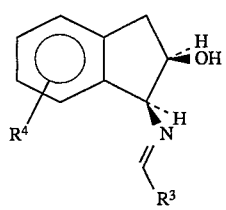

wherein $R^3$ is alkyl, aryl or heteroaryl and $R^4$ is hydrogen, alkyl, aryl, halo, nitro or alkoxy. In a preferred embodiment $R^3$ is phenyl, furan or pyrrole and $R^4$ is hydrogen.

In another aspect, the invention relates to a compound of formula II

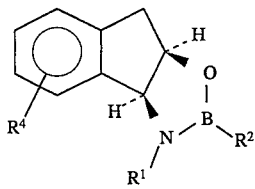

wherein $R^1$ is hydrogen, alkyl, arylmethylene or heteroarylmethylene; $R^2$ is alkyl, benzyl, phenyl or substituted phenyl; and $R^4$ is hydrogen, alkyl, aryl, halo, nitro or alkoxy; with the proviso that both of $R^1$ and $R^2$ cannot be hydrogen. In one embodiment $R^2$ and $R^4$ are both hydrogen; in another embodiment $R^1$ is hydrogen and $R^2$ is methyl, butyl or phenyl; in another embodiment $R^1$ is benzyl or heteroaryl methylene; and in another embodiment $R^2$ and $R^4$ are both hydrogen.

In another aspect, the invention relates to novel compounds of formula Ia

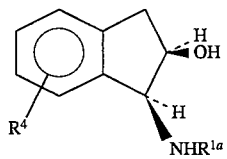

wherein $R^{1a}$ is heteroarylmethylene; and $R^4$ is hydrogen, alkyl, aryl, halo, nitro or alkoxy. Preferably, $R^1$ is pyrrolylmethyl or furanylmethyl and $R^4$ is hydrogen.

"Alkyl", as used above, refers to saturated hydrocarbon residues containing eight or fewer carbons in straight or branched chains, as well as cyclic structures. "Alkoxy" refers to the same residues, containing, in addition, an oxygen atom at the point of attachment. "Aryl" includes phenyl, substituted phenyl, naphthyl and the like; "heteroaryl" means a 5- or 6-membered aromatic heterocyclic group containing up to three heteroatoms, each selected from N, O and S. Examples include, but are not limited to thiazolyl, oxazolyl, pyridyl, furanyl, pyrrolyl, thienyl and the like. A "prochiral ketone", denoted by $R^6R^7CO$, is a ketone in which the substituents $R^6$ and $R^7$ are non-identical, so that the secondary alcohol reduction product has a chiral center at the alcohol carbon.

The graphic representations of racemic, ambiscalemic and scalemic or enantiomerically pure compounds used herein are taken from Maehr J. Chem. Ed. 62, 114–120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration. Thus, the formulas I, II and III above are intended to encompass both of the pure enantiomers of that pair:

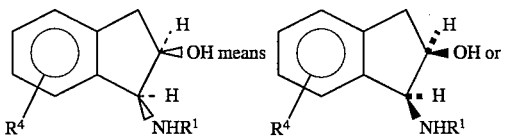

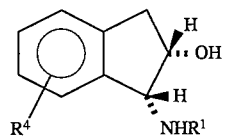

The term "enantiomeric excess" is well known in the art and is defined for a resolution of ab→a+b as $$ee_a = \left( \frac{\text{conc. of } a - \text{conc. of } b}{\text{conc. of } a + \text{conc. of } b} \right) \times 100$$

The term "enantiomeric excess" is related to the older term "optical purity" in that both are measures of the same phenomenon. The value of ee will be a number from 0 to 100, zero being racemic and 100 being pure, single enantiomer. A compound which in the past might have been called 98% optically pure is now more precisely described as 96% ee.; in other words, a 90% e.e. reflects the presence of 95% of one enantiomer and 5% of the other in the material in question.

"Catalytically effective" refers to a substoichiometric amount of indanol, which, however, is sufficient to facilitate the enantioselective conversion of a ketone to the desired alcohol. Commonly, about 10 mol % of 1-amino-2-indanol will be catalytically effective.

A preferred group of compounds of this invention is the group of the compounds of formula I and/or formula II having the S,R configuration. A second preferred group of compounds of this invention is the group of the compounds of formula I and/or formula II having the R,S configuration.

For convenience, the catalysts of the invention will often be referred to in the text as "oxazaborolidines"; in fact, following strict Chemical Abstracts nomenclature, they would be named as reduced derivatives of indeno-oxazaborole, the "idine" suffix conveying the same oxidation state as the "tetrahydro" substituent nomenclature.

DETAILED DESCRIPTION OF THE INVENTION

The compounds of formula II of the present invention are readily prepared from 1-amino-2-indanols of formula I. In the case where $R^2$ is hydrogen, the oxazaborolidine can be prepared in situ from the indanol and borane. When $R^2$ is other than hydrogen, the oxazaborolidine is more readily prepared from the indanol I and the appropriate boroxine in a separate step. This procedure may also be employed when $R^2$ is hydrogen by using borane in a separate step.

Thus a single enantiomer of a 1-amino-2-indanol derivative is suspended in an inert solvent, such as tetrahydrofuran, xylene, toluene, benzene, chlorobenzene or the like, and is heated to a temperature of from about 60° C. to about boiling. The reaction mixture is then treated with borane, a trialkyl boroxine, a triarylboroxine, an alkyl boronic acid or an aryl boronic acid and is cooled to room temperature. Suitable boroxines for this reaction include boroxines of the formula V:

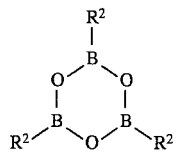

wherein $R^2$ is preferably methyl, butyl or phenyl. The reaction mixture is stirred for about one hour to about 24 hours, preferably for about 18 hours at reflux. The oxazaborolidine compound of formula I is then isolated by the removal of water and excess boroxine where necessary and utilizing the standard techniques well known to one of ordinary skill in the art of synthetic organic chemistry.

The cis 1-amino-2-indanol derivative can be prepared using well known chemistry. Cyclic cis-1-amino-2-alkanols are commonly prepared from the corresponding trans-1-amino-alkanols, which are synthetically much more accessible. For example, Lutz and Wayland have described the preparation of racemic cis-1-amino-2-indanol from racemic trans-1-amino-2-indanol in three steps (R. E. Lutz and R. L. Wayland, Jr., J. Am. Chem. Soc. 73, 1639–1641 (1951)).

Optically pure cis-(1S,2R)-1-amino-2-indanol has also been obtained by the resolution of the corresponding L-phenylalanine amide diastereomers by chromatographic separation, followed by cleavage of the amide with sodium in ethanol (W. J. Thompson et al. J. Med. Chem. 35, 1685–1701 (1992)).

The preferred process for the preparation of cis 1-amino-2-indanols for the present invention involves reaction of a trans-1-amino-2-indanol with an acylating agent (such as an acyl halide or a carboxylic acid anhydride) to give the corresponding carboxylic amide, followed by treatment of the amide intermediate under strong acid conditions to give the desired cis-1-amino-2-indanol in good yield and in only two steps.

Trans-1-amino-2-alkanols are advantageously prepared by the reaction of ammonia or a primary amine, such as methylamine, with the corresponding epoxide or bromohydrin according to literature methods (R. E. Lutz and R. L. Wayland, Jr. J. Am. Chem. Soc. 73, 1639–1641 (1951)). Optically pure trans-1-amino-2-indanol can be obtained by the resolution of racemic trans-1-amino-2-indanol with an optically pure chiral acid. In a preferred embodiment of the present invention, partially resolved trans-1-amino-2-indanol is obtained by the reaction of ammonia with partially resolved indene oxide which itself can be made by the asymmetric epoxidation of indene by any of a number of procedures known in the art. A particularly effective procedure utilizes sodium hypochlorite [E. N. Jacobsen et al. J. Am. Chem. Soc. 113, 7063–7064 (1991) and references therein)]. A preferred catalyst for the chiral oxidation is the salen of formula VI

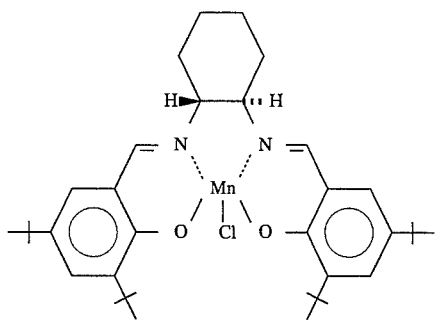

The particular salen shown is of the R,R configuration and provides 80–85% ee of the (1R,2S)-epoxide which can be carried on to the predominantly (S,S)-trans-aminoalcohol. Use of the S,S-salen provides the corresponding (1S,2R)-epoxide in similar fashion.

The benzamide of partially resolved trans-1-amino-2-indanol can be conveniently prepared from the partially resolved indene oxide by reaction of the indene oxide with aqueous ammonia followed by reaction with benzoyl chloride in the presence of a base such as NaOH using the Schotten-Baumann procedure without isolation of the trans-1-amino-2-indanol intermediate. Partially resolved trans-benzamide of trans-1-amino-2-indanol can be enriched to optically pure trans-benzamide by crystallization from an organic solvent such as ethanol (EtOH) or methanol (MeOH) or solvent mixture such as MeOH-dimethylformamide (DMF) or EtOH-DMF.

The boroxine derivatives (V) used herein are also readily prepared when not readily available. Reaction of a trialkyl- or triarylborane with boron oxide under reflux for about 24 hours to about 48 hours in an inert atmosphere conveniently prepares the trialkyl or triarylboroxine derivatives. Alternatively, reaction of borane, a trialkyl borate or a triarylborate with a suitable Grignard reagent of the formula $R^2$—Mg—X (wherein $R^2$ is as defined earlier) in a suitable inert solvent (such as tetrahydrofuran or diethyl ether) at about –20° C. to about 50° C. affords the $R^2$-substituted boronic acid upon workup. Continued reflux utilizing a Dean-Stark trap to remove water generates the $R^2$-substituted boroxine derivative.

The boronic acids which are used herein are prepared as described in the foregoing paragraph or are prepared by the method recited by Corey, supra, or according to the references cited therein.

The process of the present invention is carried out by reacting a prochiral ketone of the formula $R^6R^7CO$ with a borane reducing agent in the presence of a chiral oxazaborolidine catalyst according to formula I. The process results in the enantioselective reduction of the prochiral ketone, such that one of two possible alcohol enantiomers is formed in preference to the corresponding enantiomer. The degree of enantioselectivity will vary depending upon the size of the $R^6$ and $R^7$ groups attached to the carbonyl group of the prochiral ketone. When the $R^6$ and $R^7$ groups are similar in size, the degree of enantioselection will be lower. As the groups become increasingly disparate in size, the degree of enantioselection will be greater. However, it should be understood that the size of the $R^6$ and $R^7$ groups is not the sole determining factor affecting the degree of enantioselectivity achieved. Ordinarily, with prochiral ketones wherein $R^6$ and $R^7$ are at least moderately different in size, the desired enantiomer will be obtained in at least 80% enantiomeric excess (e.e.). Usually, however, enantiomeric excesses above 90% are obtained.

The prochiral ketone is dissolved in a suitable inert solvent such as diethyl ether, dioxane, tetrahydrofuran (THF) or the like. THF is preferred. A catalytically effective amount of a chiral oxazaborolidine compound of formula II can be added to the reaction mixture at from about −78° C. to about room temperature. The preferred temperature will vary depending upon the particular borane reducing agent being used; room temperature is commonly optimal. The preferred amount of the catalyst is about 5–10 mole % with respect to the ketone. The reaction mixture is then treated slowly with about 2.1 hydride equivalents of a borane reducing agent such as borane dimethylsulfide complex, borane tetrahydrofuran complex, catecholborane or the like.

Alternatively, the indanol catalyst precursor I or III can be dissolved in the inert solvent, followed by one equivalent of borane reducing agent to generate the catalyst mixture in situ. The ketone and an additional amount of the borane reducing agent necessary to reduce the ketone are then added to the catalyst mixture.

When the prochiral ketone contains an $R^6$ group which bears a borane-coordinating functionality, additional hydride equivalents of reducing agent are necessary. Borane-dimethylsulfide complex is generally preferred for its ease of use. Generally the reducing agent is added at a rate which modulates the rate of the catalytic reduction. The reaction is sometimes complete as soon as all of the reducing agent has been added, as can be determined by monitoring the course of the reaction by thin layer chromatography. However, occasionally it will be longer periods of time. The temperature of the reaction mixture is then adjusted to 0° C. and quenched with a proton source.

The proton source, usually a lower alkanol such as methanol (MeOH), is added slowly to prevent an exothermic reaction. The product is isolated by removing the solvent in vacuo followed by partitioning between an organic solvent and an aqueous acid followed by separation of layers and purification according to the standard techniques of organic chemistry.

The prochiral ketone may be any compound of the formula $R^6R^7CO$, wherein $R^6$ and $R^7$ are different and wherein $R^6$ and $R^7$ are inert to reduction by borane. Additionally, if enough reducing agent is utilized to account for the presence of borane coordinating substituents on $R^6$ or $R^7$, then either may be thus substituted. A "borane-coordinating substituent" is a functional group which has the ability to donate an electron pair to boron, forming a coordinate bond with the boron. Typical examples include amines and various nitrogen-containing heterocycles. Thus, $R^6$ and $R^7$ may be any organic radicals (e.g. alkyl, aryl, alkenyl) and may be taken together to form a ring system so that $R^6R^7CO$ is cyclic. Additionally, $R^6$ and $R^7$ may be independently substituted. It will be understood by one of ordinary skill in the art that when $R^6$ or $R^7$ contains an alkenyl substituent it will be necessary to choose a borane reducing agent which is not capable of hydroborating the olefin.

Products from the reduction of prochiral ketones of formula IV ($R^5$=Br or Cl) are important intermediates for preparation of chiral pharmaceuticals. For example, the halohydrin product is converted to the corresponding epoxide by treatment with base. The m-chlorostyrene epoxide has been used in the synthesis of CL316,243, a compound useful in the treatment of hyperglycemia.

The present invention is illustrated by the following examples. However, it should be understood that the invention is not limited to the specific details of these examples.

All reactions are conducted under an inert atmosphere, such as nitrogen or argon, unless otherwise specified. All solvents are anhydrous, i.e., contain such a small amount of water that the water does not interact with the reagents, intermediates or products so as to adversely affect the yield of the desired products.

PREPARATION OF CATALYSTS

Example 1

Cis-(1S,2R)-1-amino-2-indanol

A 5-L three neck Morton-type flask equipped with an overhead stirrer, an addition funnel and a thermometer was charged with 2.5 L of NaOCl (10% aq, 2.0 eq, 4.0 mol). The solution was cooled to ca. 5°–10° C. A solution of (R,R)-Mn-Salen catalyst X [E.N. Jacobsen et al. *J. Am. Chem. Soc.* 113, 7063–7064 (1991)] (19.1 g, 0.015 eq, 0.03 mol) in 150 mL of $CH_2Cl_2$ was added, followed by a solution of indene (260 mL, 1.0 eq, 2.0 mol) in 100 mL of $CH_2Cl_2$ at 5°–10° C. The mixture was stirred vigorously at 5°–10° C. for 4 hr. Heptane (1.4 L) and Celite (40 g) were added and the mixture stirred for 40 min without cooling. The mixture was filtered and the flask and the solid cake were washed with 200 mL of heptane.

The combined filtrates containing partially resolved indene oxide were concentrated to ca. 400 mL and the concentrate treated with 1.4 L of aqueous ammonia (28% aq.) in 600 mL of MeOH in the presence of 20 g of Celite at 25°–30° C. for 15 hr. The MeOH and excess of ammonia were removed by distillation over a period of 4–5 hr until the pot temperature reached 90° C. Water (550 mL) was added and the hot mixture filtered. The flask and solid filter cake were washed with ca. 400 mL of hot water. The combined filtrates were placed under vacuum for 40 min to remove remaining ammonia and transferred to a 5-L Morton-type flask.

The above solution, containing partially resolved trans-(1S,2S)-1-amino-2-indanol, was cooled to ca. 15°–25° C. and NaOH (50% aq., 192 g) and acetone (800 mL) were added. Benzoyl chloride (1.2 eq, 2.4 mol, 280 mL) was added at 15°–25° C. over 1 hr and the resulting slurry stirred at 20°–25° C. for 2 hr. The mixture was filtered and the solid washed with 400 mL of acetone-water (1:1, v/v) and recovered as crude trans-benzamide of partially resolved trans-(1S,2 S)-1-amino-2-indanol.

The crude benzamide (ca. 464 g) was dissolved in 1125 mL of DMF at 90° C. and MeOH (750 mL) was added at 80°–86° C. over 1 hour to the DMF solution. The solution was slowly cooled to 0°–5° C. over 1.5 h and held at 0°–5° C. for 2 h. The solid was recovered by filtration, washed with 500 mL cold (0°–5° C.) MeOH and dried under vacuum at 40° C. to give optically pure trans-benzamide of trans-(1S, 2S)-1-amino-2-indanol as pale yellow crystals (240 g, 47% yield from indene, 99% ee, m.p. 232° C.).

A mixture of the trans-benzamide (90 g, 355 mmol) and 227 g of 80% wt $H_2SO_4$ was heated at 80°–85° C. for 1 h. The mixture was treated with 377 mL of water and heated to 100°–115° C. for 3.5 h. The mixture was cooled to 30°–35° C. and washed with 355 mL of $CH_2Cl_2$. The aqueous solution was then neutralized with 370 g of 50% NaOH at <50° C., and 175 mL water was added to dissolve the inorganic salts ($Na_2SO_4$). The aqueous mixture was extracted with 535 mL of $CH_2Cl_2$ at 30°–35° C., and the $CH_2Cl_2$ extracts decolorized with 4.5 g activated carbon and dried with 7.5 g $MgSO_4$ (anhydrous). The mixture was filtered through Celite and the filter cake washed with 100 mL of $CH_2Cl_2$. The combined filtrates were concentrated to ca. 450 mL and 215 mL heptane was added at 40° C. over 30 min. The solution was cooled to 0°–5° C. and the resulting solid recovered by filtration affording cis-(1S,2R)-1-amino-2-indanol (45.2 g, 84%>99.5% ee).

Examples 2a–2i

N-alkyl-cis-1-amino-2-indanol derivatives:

Compounds of formula I ($R^1 \neq H$) are prepared by the reductive alkylation of cis-1-amino-2-indanol with an aldehyde or ketone using a hydride reducing agent such as $NaBH_4$, $NaBH(OAc)_3$ and $NaBH_3CN$, or by catalytic reductive alkylation of cis-1-amino-2-indanol with an aldehyde using hydrogen in the presence of heterogenous catalyst such as Pd/C or Raney Ni. The general procedure for using $NaBH(OAc)_3$ is as follows: Sodium triacetoxyborohydride (1.5 eq) is added to a mixture of cis-1-amino-2-indanol (1.0 eq), the aldehyde (1.0 eq) and acetic acid (1.5 eq) in THF (0.2–0.3M in aminoindanol) at ambient temperature. The resulting mixture is stirred until the aldehyde is consumed (3–15 h). The mixture is then concentrated to remove most of the solvent (THF) and the residue is quenched with water. After adjusting the pH to 11–12 with a solution of NaOH, the product precipitates out from the solution. The product is then collected by filtration and recrystallized. The product can also be extracted into an organic solvent such as ethyl acetate and washed with a solution of $NaHCO_3$ and NaCl. After removal of solvent, the product is recrystallized to give the N-alkylated cis-aminoindanol in 60–90% yield.

Typical examples are shown in Table I.

TABLE I

| Example | $R^1=$ | Starting Aldehyde or ketone | Yield % | rex Solvent |
| --- | --- | --- | --- | --- |
| 2a | iPr | acetone | 70 | heptane |
| 2b | iBu | isobutyraldehyde | 91 | heptane |
| 2c | $cC_6H_{11}$ | cyclohexanone | 90 | heptane |
| 2d | $cC_6H_{11}$—$CH_2$— | cyclohexane carboxaldehyde | 74 | EtOAc/ heptane |
| 2e | $PhCH_2$— | benzaldehyde | 77 | MeOtBu |
| 2f | 2-pyrrolyl-methyl | pyrrole-2-carbox-aldehyde | 81 | EtOAc/ heptane |
| 2g | 2-pyridinyl-methyl | pyridine-2-carbox-aldehyde | 60 | MeOtBu |
| 2h | $Cp_2FeCH_2$— | ferrocene carbox-aldehyde | 79 | THF/heptane |
| 2i | 2-thienylmethyl | thiophene-2-carboxaldehyde | 80 | EtOAc/ heptane |

Example 3

Oxazaborolidine II

3a Oxazaborolidine II ($R^1=R^4=H$; $R^2=Me$)

A 50 mL, 3-necked flask was equipped with a stirring bar, a distillation head and a thermometer. To the reaction flask were added 746 mg of (1S,2R)-aminoindanol (I) (5.0 mmol, 1.0 eq.) and 25 mL of anhydrous toluene at room temperature. The mixture was heated to 80° C. with stirring and 0.454 mL of trimethylboroxine (3.25 mmol, 0.65 eq.) was added in one portion. The oil bath was removed and the reaction mixture stirred at room temperature for 18 hours. The solution was concentrated to a volume of 10 mL. Ten milliliters of anhydrous toluene was added and distilled out under normal atmosphere. This process was repeated once more and the residue further distilled to dryness at reduced pressure (45°–55° C./110–130 mmHg). Ten milliliters of dry toluene was added into the flask to make a 0.5M solution of the catalyst. The catalyst prepared in this way has been used for asymmetric reductions and is stable for at least six weeks at 5° C.

3b Oxazaborolidine II ($R^1$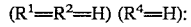$R^4=$H, $R^2=$nBu)

A 50 mL, 3-necked flask was equipped with a stirring bar, a Dean-Stark tube attached with a reflux condenser and a thermometer under nitrogen. To the reaction flask were added 746 mg of (1S,2R)-aminoindanol (I) (5.0 mmol, 1.0 eq.) and 25 mL of anhydrous toluene at room temperature. Five hundred ten milligrams of n-butylboronic acid (5.0 mmol, 1.0 eq.) was added dropwise at room temperature. The mixture was heated under reflux for 24 hours and then concentrated to a volume of 10 mL under 1 atm. Ten milliliters of anhydrous toluene was added and distilled out under normal atmosphere. This process was repeated once more and the residue further distilled to dryness at reduced pressure (45°–55° C./110–130 mmHg). The residue was diluted to a volume of 10 mL with anhydrous toluene to make a 0.5M solution of the catalyst.

3c Oxazaborolidine II ($R^1=R^4=H$, $R^2=$phenyl)

A 50 mL, 3-necked flask was equipped with a stirring bar, a distillation head, and a thermometer under nitrogen. To the reaction flask were added 746 mg of (1S,2R)-aminoindanol (I) (5.0 mmol, 1.0 eq.) and 25 mL of anhydrous toluene at room temperature. The mixture was cooled to 0° C. with stirring and 0.649 mL of dichlorophenylborane (5.0 mmol, 1 eq.) was added dropwise. The cooling bath was removed and the reaction mixture stirred at room temperature for 12 hours. The solution was concentrated to a volume of 10 mL under 1 atm. Ten milliliters of anhydrous toluene was added and distilled out under normal atmosphere. This process was repeated once more and the residue was distilled to dryness at reduced pressure (45°–55° C./110–130 mmHg). The residue was diluted to a volume of 10 mL with anhydrous toluene to make a 0.5M solution of the catalyst.

| Example 4 | Iminoindanols III |
| --- | --- |
| 4a | Iminoindanol III ($R^3$ = 2-pyrrolyl) |
| 4b | Iminoindanol III ($R^3$ = 2-furanyl) |
| 4c | Iminoindanol III ($R^3$ = 2-thiophenyl) |

The general procedure for preparation of compound of formula (III) is as follows: A mixture of cis-1-amino-2-indanol (1.0 eq) and the aldehyde (e.g. pyrrole-2-carboxaldehyde) (1.0 eq) in anhydrous EtOH is heated at reflux until no aldehyde is left. The concentrated and the resulting solids are recrystallized to give the cis-1-imino-2-indanols derivates. Yields were: 4a, 65% from MeOH/EtOAc; 4b, 42% from EtOAc/heptane; 4c, 61% from EtOAc/heptane.

REDUCTIONS

GENERAL METHOD A: Asymmetric reduction catalyzed by aminoindanol-BH complex (IIa) prepared in situ.

($R^1=R^2=$H) ($R^4=$H):

A 25 mL, 3-necked flask is equipped with a stirring bar and a thermometer. To the reaction flask at room temperature are added 14.9 mg of (1S,2R)-aminoindanol (0.1 mmol, 10 mol %) and 3 mL of anhydrous THF. Twenty microliters of $BH_3.DMS$ (10M in DMS, 0.2 mmol, 0.2 eq.) is added dropwise and the resulting mixture is stirred for 16 h at room temperature. After that, a solution of 1.0 mmol of ketone (1.0 eq.) in 1.5 mL of anhydrous THF and a solution of 0.8 mmol of $BH_3.DMS$ (0.08 mL, 0.8 eq) in 1.42 ml of THF are simultaneously added into the flask via a syringe pump over 1–3 hours at 0° C. to room temperature. The mixture is stirred at that temperature for 1 to 3 hours and quenched with 2 mL of MeOH. The mixture is dried in vacuo and diluted with 10 mL of hexane/ethyl acetate (5:1). The organic solution is washed with 3×3 mL of cold 2% $H_2SO_4$. After filtration, the solvents are removed in vacuo and the residue is further dried under high vacuum for 1 hour to provide the crude product in 98– 100% yield. Enantiomeric purity is determined by HPLC analysis on chiral column. It has been found that a decrease to 5 mol % of the catalyst still gives excellent results in both chemical yield and ee.

EXAMPLES

A1. 2-Chloroacetophenone to (S)-1-phenyl-2-chloroethanol, 98% yield, 91.7% ee.

A2. m-Chloro-2-bromoacetophenone to (S)-1-(3 -chlorophenyl)-2-bromoethanol, 99% yield, 90% ee.

General Method A': Asymmetric reduction using catalyst II ($R^4$=H, $R^2$=H, $R^1$=alkyl):

Catalyst II (0.2 mmol) is dissolved in anhydrous THF (7 mL) at 25° C. Borane-DMS (2.0 mmol, 0.2 mL) is added to the solution. The resulting solution is stirred at 25° C. for about 15 to 16 hours. A solution of the ketone (2.0 mmol) in 3 mL of anhydrous THF is added to the solution with ice water cooling over 5 to 10 minutes. The resulting solution is stirred at 25° C. until all ketone is consumed (about 3 hours) and the reaction is worked up as General Method A.

EXAMPLES

A3. m-Chloro-2-bromoacetophenone to (S)-1-(3 -chlorophenyl)-2-bromoethanol, 98% yield, 89% ee using II, $R^1$=cyclohexylmethyl.

A4. m-Chloro-2-bromoacetophenone to (S)-1-(3 -chlorophenyl)-2-bromoethanol, 98% yield, 85% ee using II, $R^1$=isopropyl.

A5. m-Chloro-2-bromoacetophenone to (S)-1-(3 -chlorophenyl)-2-bromoethanol, 98% yield, 78% ee using II, $R^1$=2-pyrrolylmethyl.

General Method B: Asymmetric reduction using catalyst II ($R^2$=alkyl; $R^1$=$R^4$=H)

A 25 mL, 3-necked flask is equipped with a stirring bar, a thermometer and a rubber septum. 0.06 mL of 0.5M catalyst solution (0.3 mmol, 10 mol %) is added to the reaction flask containing 3 mL of dry THF. To the solution at room temperature is added 60 mL of 10.0M $BH_3$.DMS solution in DMS (0.6 mmol, 0.2 eq.) The resulting mixture is stirred at room temperature for 30 min and then cooled to −20° C. A solution of 3.0 mmol of ketone in 3 mL of anhydrous THF and a solution of 2.4 mmol of $BH_3$.DMS (10M, 0.240 mL, 0.8 eq) in 2.76 mL THF are simultaneously added into the flask via a syringe pump over 3 hours at 0° to −20° C. After the addition, the mixture is stirred for 30 min at that temperature and quenched with 3 mL of MeOH. The mixture is warmed to room temperature and concentrated to dryness in vacuo. Twenty milliliters of hexane/ethyl acetate (5:1) is added to dilute the crude product. The organic solution is washed with 3×5 mL of cold 2% $H_2SO_4$ (5° C.), then 10 mL of saturated $NaHCO_3$ solution and dried over anhydrous $Na_2SO_4$. After filtration, the solvents are removed in vacuo and the residue is further dried under high vacuum for 1 hour to give the alcohol product.

EXAMPLES

Catalyst II ($R^1$=$R^4$=H; $R^2$=methyl)

B1. 2-Chloroacetophenone to (S)-1-phenyl-2-chloroethanol, 99% yield, 96% ee.

B2. 2-Chloroacetophenone to (R)-1-phenyl-2 -chloroethanol, 99% yield, 96% ee.

B3. m-Chloro-2-bromoacetophenone to (S)-1-(3 -chlorophenyl)-2-bromoethanol, 99% yield, 95.5% ee.

B4. m-Chloro-2-bromoacetophenone to (R)-1-(3 -chlorophenyl)-2-bromoethanol, 99% yield, 95.5% ee.

B5. m-Chloro-2-chloroacetophenone to (S)-1-(3 -chlorophenyl)-2-chloroethanol, 99% yield, 94% ee.

B6. m-Chloro-2-chloroacetophenone to (R)-1-(3 -chlorophenyl)-2-chloroethanol, 99% yield, 94% ee.

B7. Acetophenone to (S)-1-phenylethanol, 98% yield, 86% ee.

B8. Acetophenone to (R)-1-phenylethanol, 98% yield, 86% ee.

Catalyst II ($R^1$=$R^4$=H, $R^2$=n-butyl)

B9. m-chloro-2-bromoacetophenone to (S)-1-(3 -chlorophenyl)-2-bromoethanol, 97% yield, 96% ee.

Catalyst II ($R^1$=$R^2$=H, $R^2$=phenyl)

B10. m-Chloro-2-bromoacetophenone to (S)-1-(3 -chlorophenyl)-2-bromoethanol, 99% yield, 93% ee

General Method B'

Same as General Method B except Catalyst II: ($R^4$=H; $R^2$=methyl; $R^1$=alkyl)

B11. 2-chloroacetophenone to (S)-1-phenyl-2-chloroethanol, 98% yield using II ($R^1$=cyclohexylmethyl $R^2$=methyl.

B12. 2-chloroacetophenone to (S)-1-phenyl-2-chloroethanol, 99% yield, 89% ee using II ($R^1$=isobutyl, $R^2$=methyl).

B13. 2-chloroacetophenone to (S)-1-phenyl-2-chloroethanol, 98% yield, 89% ee using II ($R^1$=2-pyrrolylmethyl, $R^2$=methyl).

General Method C

Asymmetric reduction using catalyst III ($R^3$=2 -pyrrole; $R^1$=$R^4$=H)

The reduction of α-bromo-3-chloroacetophenone with the pyrrole-2-carboxaldehyde-derived ligand is as follows: A solution of the imine alcohol (0.023 g, 0.1 mmol, 0.1 eq) derived from the reaction of cis-(1S,2R)-1-amino-2-indanol and pyrrole-2carboxaldehyde was stirred with borane dimethyl sulfide complex (10M, 0.1 mL, 1.0 mmol, 1.0 eq) in 7 mL of dry THF for 12 hours at room temperature. A solution of m-chloro-α-bromoacetophenone (0.23 g, 1.0 mmol, 1.0 eq) in 3 mL of THF was added to the above solution at room temperature over 10 min. The resulting solution was stirred at room temperature for 2 hours until no ketone was left. After normal workup, the resulting alcohol was obtained in >98% yield and 86% ee.

Enantiomeric excess was determined by HPLC on Chiralcel OJ column; mobile phase, hexane/i-PrOH (95:5); flow rate, 0.4 to 1.0 mL/min; UV, 220 nm. The absolute configurations were determined by comparison of optical rotations with those of the authentic compounds.

The catalysts of the invention were compared with the known (Corey) pyrrolo-oxazaborolidine catalyst in the reduction of three typical substrates. The catalysts were present at 10 mol % and the reaction was carried out at −20°

C. with simultaneous addition of borane and substrate over three hours. The results are shown below. The top row presents the structures of the test substrates and the left side presents the structures of the catalysts. The ee's are shown in the appropriate columns and rows according to catalyst and substrate.

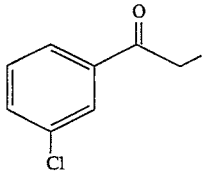

The catalysts of the invention are in some cases equivalent to the known catalyst and in some cases superior.

We claim:

1. A method for the enantiospecific reduction of a prochiral ketone to the corresponding alcohol comprising reacting said prochiral ketone with a borane reducing agent in an inert solvent in the presence of a catalytic amount which is a substoichiometric amount sufficient to effect the enantioselective conversion of said ketone to said alcohol, of a compound chosen from the group consisting of

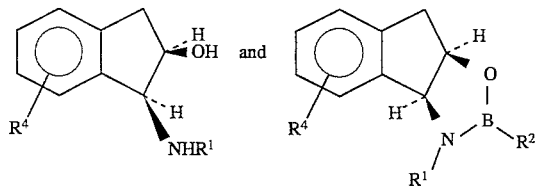

wherein $R^1$ is hydrogen, alkyl, arylmethylene or heteroarylmethylene; heteroaryl is a 5- or 6-membered aromatic heterocyclic group containing up to three heteroatoms independently selected from the group consisting of N, O and S;

$R^2$ is; alkyl, benzyl, phenyl or substituted phenyl; and $R^4$ is hydrogen, alkyl, aryl, halo, nitro or alkoxy.

2. A method according to claim 1 wherein said borane reducing agent is borane-methyl sulfide or borane-THF.

3. A method according to claim 1 wherein $R^2$ is hydrogen, methyl, butyl or phenyl and $R^4$ is hydrogen.

4. A method according to claim 1 wherein $R^1$ is hydrogen and $R^2$ is hydrogen, methyl, butyl or phenyl.

5. A method according to claim 1 wherein said ketone is of the formula

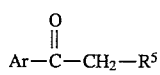

wherein Ar is aryl or substituted aryl and $R^5$ is hydrogen or halogen.

6. A method according to claim 5 wherein Ar is phenyl, alkylphenyl, chlorophenyl, hydroxyphenyl, alkoxyphenyl, nitrophenyl or naphthyl.

7. A process for the enantioselective reduction of a prochiral ketone comprising (a) combining at least one equivalent of a borane reducing agent with a compound of formula

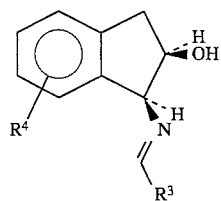

wherein $R^3$ is alkyl, aryl or a 5- or 6membered aromatic heterocyclic group containing up to three heteroatoms independently selected from the group consisting of N, O and S and $R^4$ is hydrogen, alkyl, aryl, halo or alkoxy, in an inert solvent to provide a catalyst mixture; and (b) adding more than one equivalent of a prochiral ketone and a corresponding amount of a borane reducing agent to said catalyst mixture.

8. A process according to claim 7 wherein said borane reducing agent is borane-methyl sulfide or borane-THF.

9. A process according to claim 7 wherein $R^3$ is phenyl, furanyl or pyrrolyl.

10. A process according to claim 7 wherein said ketone is of the formula

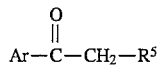

wherein Ar is aryl or substituted aryl and $R^5$ is hydrogen or halogen.

11. A process according to claim 10 wherein Ar is phenyl, alkylphenyl, chlorophenyl, hydroxyphenyl, alkoxyphenyl, nitrophenyl or naphthyl.

* * * * *

UNITED STATES PATENT AND TRADEMARK OFFICE
CERTIFICATE OF CORRECTION

PATENT NO. : 5,495,054
DATED : Feb. 27, 1996
INVENTOR(S) : Gao et al.

It is certified that error appears in the above-indentified patent and that said Letters Patent is hereby corrected as shown below:

Col. 13 Claim 1, line 53, after $R^2$ is; insert --hydrogen--.

Col. 14 Claim 7, line 42, delete 6membered and insert therefor --6-membered--.

Signed and Sealed this

Twenty-first Day of May, 1996

Attest:

BRUCE LEHMAN

Attesting Officer      Commissioner of Patents and Trademarks

UNITED STATES PATENT AND TRADEMARK OFFICE
CERTIFICATE OF CORRECTION

PATENT NO. : 5,495,054
DATED : Feb. 27, 1996
INVENTOR(S) : Gao et al.

It is certified that error appears in the above-indentified patent and that said Letters Patent is hereby corrected as shown below:

On the title page, item [57], in the Abstract and the following columns. Replace the solid wedge with an open wedge in the structures.

column 2, lines 10, 15 and 45;
   Column 3, lines 5, 15 and 35;
   column 13, claim 1, line 40; and
   column 14, claim 7, line 35.

Signed and Sealed this

Third Day of September, 1996

Attest:

BRUCE LEHMAN

*Attesting Officer*  *Commissioner of Patents and Trademarks*